United States Patent [19]

Ushizawa et al.

[11] Patent Number: 5,085,989
[45] Date of Patent: Feb. 4, 1992

[54] METHOD AND REAGENT FOR QUANTITATIVE ANALYSIS OF 3-OXO-5β-STEROID

[75] Inventors: Koji Ushizawa; Takae Shigihara; Akemichi Maki; Toshiyuki Akimoto; Senkichi Nagasaki; Miyoshi Hirata, all of Tokyo, Japan

[73] Assignee: Daiichi Pure Chemicals Co., Ltd., Tokyo, Japan

[21] Appl. No.: 574,525

[22] Filed: Aug. 28, 1990

Related U.S. Application Data

[63] Continuation of Ser. No. 80,918, Aug. 3, 1987, abandoned.

Foreign Application Priority Data

Nov. 11, 1986 [JP] Japan .................. 61-268313

[51] Int. Cl.$^5$ .................. C12Q 1/26; C12Q 1/32
[52] U.S. Cl. .................. 435/26; 435/25
[58] Field of Search .................. 435/25, 26

[56] References Cited

U.S. PATENT DOCUMENTS 3,791,933  2/1974  Moyer et al. .................. 195/127
4,816,394  3/1989  Ushizawa et al. .................. 435/26

OTHER PUBLICATIONS

Christiansen et al., Chemical Abstracts, 103:84307m, 9/16/85, p. 303.
Chemical Abstracts, vol. 107, No. 13, Sept. 28, 1987, p. 306 abstract No. 111955n.
Chemical Abstract, vol. 76, No. 13, Mar. 27, 1972, p. 138 abstract No. 69430b.
Comprehensive Biochemistry, vol. 13, 3rd Ed., pp. 80, 81 Florkin et al.

*Primary Examiner*—David M. Naff
*Attorney, Agent, or Firm*—Oblon, Spivak, McClelland, Maier & Neustadt

[57] ABSTRACT

A quantitative analysis of 3-oxo-5β-steroid is carried out by acting 3-oxo-5β-steroidΔ$^4$-dehydrogenase on a sample in the presence of a reducing chromophoric agent, and measuring the optical density of the chromophoric substance thereby produced. A typical reducing chromophoric agent is a tetrazolium compound. The invention also provides a reagent for the quantitative analysis of 3-oxo-5β-steroid comprising 3-oxo-5β-steroidΔ$^4$-dehydrogenase and a tetrazolium compound. The analysis and reagent provide a simple and reliable method for a liver function test.

6 Claims, 1 Drawing Sheet

METHOD AND REAGENT FOR QUANTITATIVE ANALYSIS OF 3-OXO-5β-STEROID

This application is a continuation of application Ser. No. 07/080,918, filed on Aug. 3, 1987, now abandoned.

BACKGROUND OF THE INVENTION

1. Field of the Invention

This invention relates to a quantitative analysis of 3-oxo-5β-steroid by means of an enzymatic method and a reagent therefor.

2. Description of the Background

Among liver function tests those using bile acids have attained an important position in a clinical diagnosis of liver and/or biliary tract diseases in the past several years because of the wide acceptance of the quantitation of the total bile acids in serum employing 3α-hydroxysteroid-dehydrogenase.

There has been known for long time, as a liver function test, a loading test conducted by measuring the metabolic rate, after administration of dehydrochoric acid which is a typical of 3-oxo-5β-steroid to the body of a subject [J. Japan Internal Medicine, 21, 567 (1933)]. The clinical efficiency of this test can be explained as follows. Namely, dehydrochoric acid administered either orally or otherwise at normal or healthy conditions of a subject is partly transferred to the kidney without being captured at the liver and excreted in urine as it is, but the most of the dehydrochoric acid is captured at the liver, reduced to the reduced form of dehydrochoric acid, and excreted in bile. The reduced form of dehydrochoric acid thus excreted in bile is absorbed at intestine and taken into blood, transferred to kidney, and then excreted into urine. If there are any disorders in the liver function of the subject, only partial reduction of dehydrochoric acid occurs thus giving rise to increased excretion of dehydrochoric acid and decreased excretion of reduced form of dehydrochoric acid in urine as compared to a person with a normal liver function. Likewise, the dehydrochoric acid concentration in blood decreases rapidly if the liver functions with a normal hepatic reduction. The rate of decrease in the blood dehydrochoric acid level lowers as the liver function degrades. The measurement of this function is important in order to determine the reduction-detoxication of the liver.

The quantitative analysis of dehydrochoric acid has been studied since 1930's. The methods of analysis include those employing paper chromatography, thin-layer chromatography, high performance liquid chromatography and the like [J. Yonago Physic, 3, 64 (1951); J. Biochem. 29, 271 (1934)]. The method of tracing labeled dehydrochoric acid has also been proposed [(J. Clin. Invest. 52, 715 (1973)]. These methods are carried out according to the following procedures. When serum is employed as a sample, 1–2 ml of a serum sample is diluted with 9 times by volume of 0.1 N - NaOH physiological saline and passed through a column of Amberlite XAD-2 or the like filler. The column is washed with distilled water and eluted with ethanol to obtain an ethanol solution of bile acids, which is then concentrated by means of an evaporator. The concentrate thus obtained is developed by thin layer chromatography or paper chromatography for separation, using a developing solvent of, for example, butanol/acetic acid/water (10:1:1). The detection limit of this method is approximately 10 μg. When an isotope is employed, a 24-hour urine sample, for instance, is passed through the aforementioned column, extracted with ethanol, concentrated, developed by paper chromatography for separation, and then the quantity of the radio isotope is measured. The detection limit is in the range from 1 μg to 100 μg.

These methods, however, are not employed in a routine assay because of requirements of complicated pretreatment procedures for extraction, concentration, etc. as well as expensive equipment and materials. In particular, the poor measurement sensitivity in these methods poses following problems. That is, urine does not contain the indicative substance of the amount sufficient for the reliable assay. In case of using serum as a sample a large amount of the sample is usually needed because the dehydrochoric acid level in blood is not always sufficiently high after administration of this substance. In addition, the assay may be sometimes hindered by the other components in the serum sample. Determination using an isotope is not necessarily a preferred method because of requirement of special equipment and devices A strong need, therefore, has existed for the development of a convenient and precise quantitative analysis of 3-oxo-5β-steroid.

The inventors have conducted extensive studies for solving the aforementioned problems in the prior art. As a result, it was found that when 3-oxo-5β-steroidΔ⁴-dehydrogenase is acted on 3-oxo-5β-steroid in the presence of a reducing chromophoric agent, 3-oxo-5β-steroid is oxidized into 3-oxo-5β-Δ⁴-steroid, and at the same time, the reducing chromophoric agent is colored and may be conveniently submitted to a sensitive quantitation. The finding has led to the completion of this invention.

SUMMARY OF THE INVENTION

Accordingly, an object of this invention is to provide a quantitative analysis of 3-oxo-5β-steroid which comprises allowing 3-oxo-5β-steroidΔ⁴-dehydrogenase to act on a sample in the presence of a reducing chromophoric agent and measuring the optical density of the chromophoric substance thereby produced.

Another object of this invention is to provide a reagent for the quantitative analysis of 3-oxo-5β-steroid comprising 3-oxo-5β-steroidΔ⁴-dehydrogenase and a reducing chromophoric agent.

The reaction upon which the quantitative analysis of this invention is based is shown by the following scheme:

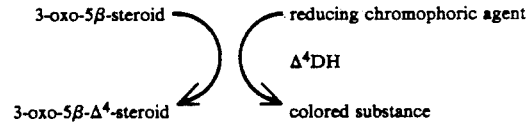

That is, the quantitative analysis of this invention can be carried out by first oxidizing 3-oxo-5β-steroid to a 3-oxo-5β-Δ⁴-steroid by the use of 3-oxo-5β-steroidΔ⁴-dehydrogenase (hereinafter abbreviated to "Δ⁴DH") in the presence of a reducible chromophoric agent, and at the same time, reducing said reducing chromophoric agent into a colored substance, and then measuring the optical density of the colored substance.

A more complete appreciation of the invention and many of the advantages thereof will be readily obtained as the same becomes better understood by reference to the following description.

Figure 1:
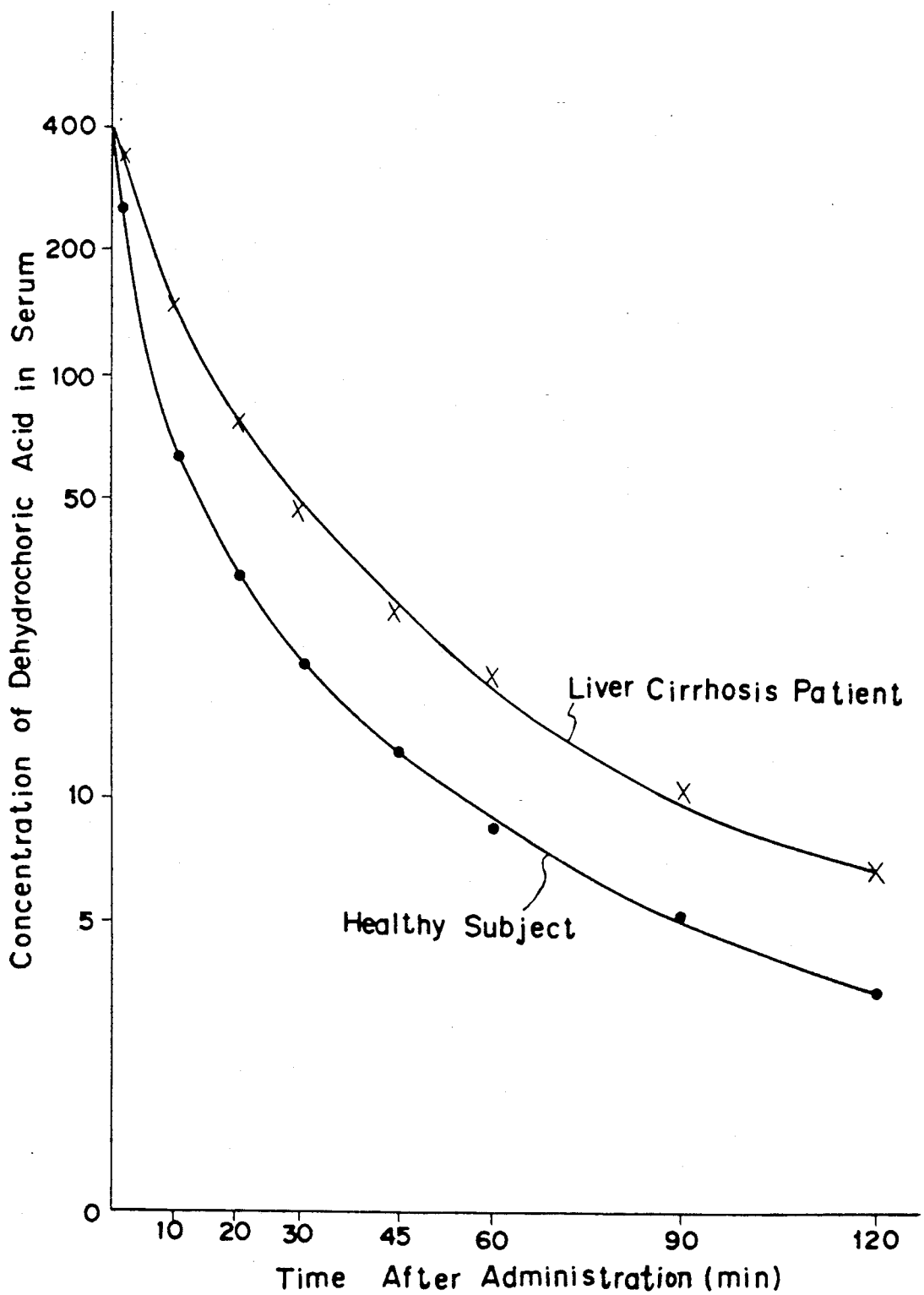
FIG. 1 is a diagram showing the changes in dehydrochoric acid level in serum on lapse of time, in which the concentration of dehydrochoric acid in serum ($\mu$mole/$\lambda$) is plotted along the ordinate and the time after administration of dehydrochoric acid (min.) is plotted along the abscissa.

DETAILED DESCRIPTION OF THE PREFERRED EMBODIMENTS $\Delta^4$-DH (EC.1. 3. 99. 6) useful in the practice of this invention is a dehydrogenase possessing a specificity to 3-oxo-5$\beta$-steroid and is widely found in microorganisms such as those belonging to the genus Pseudomonas [J. Chem. Soc.; Chem. Comm. 3, 115 (1974); J. Biol. Chem. 218, 675 (1956), ibid. 234, 2014 (1959); Biochem. Biophy. Acta 56, 584 (1962)], the genus of Arthrobactor [Eur. J. Biochem. 47, 555 (1974)]; the genus of Nocardia [Chemical and Pharmaceutical Bulletin 21, 2794 (1973), ibid. 23, 2164 (1975); Dissertation Abstracts 35, 3839 (1975)]; the genus of Corynebacterium (U.S. Pat. No. 3,639,212), etc. There is no limitation to the source of the enzyme.

The amount of $\Delta^4$-DH to be used may be, in terms of the reaction concentration, 50–10,000 units/$\lambda$, preferably 300–3,000 units/$\lambda$.

Any reducing chromophoric agents may be used for the purpose of this invention so long as their intramolecular potential may change by accepting electrons thereby producing a chromophore which is capable of absorbing radiation of only a ray with a specific wavelength. Specifically, they may be tetrazolium compounds, including but not limited to, nitroblue tetrazolium (hereinafter abbreviated as "NTB"), 3-(p-indophenyl)-2-(p-nitrophenyl)-5-phenyl-2H-tetrazolium chloride (hereinafter abbreviated as "INT"), 3-(4,5-dimethyl-2-thiazolyl)-2,5-diphenyl-2H-tetrazolium bromide (hereinafter abbreviated as "MTT") and 1,1'-(3,3'-dimethoxy-4,4'-biphenylene)-bis{5-(4-nitropheny)-3-[4-(2-hydroxy-3-(2-hydroxyethyldiethylamino)-propxoy)-phenyl]}-2H-tetrazolium chloride (hereinafter abbreviated as "W.S.NTB"). The concentration of the tetrazolium compound may be in the range of 50–2,000 $\mu$mole/$\lambda$, preferably, 100–1,000 $\mu$mole/$\lambda$.

As 3-oxo-5$\beta$-steroid to which the quantitative analysis of this invention is applicable may be, beside dehydrochoric acid, 5$\beta$-androstan-3,17-dione, $\Delta^1$-5$\beta$-androstene-3,17-dione, 5$\beta$-pregnane-3,20-dione, 21-hydroxy-5$\beta$-pregnane-3,20-dione, etc. Samples usable for the analysis may, therefore, be serum, plasma, urine and the like.

In practicing the quantitative analysis of this invention, the sample, reducing chromophoric agent and $\Delta^4$DH may be added in an arbitrary order to a buffer, and after reaction the optical density of the reaction solution is measured.

Any conventional buffers may be used for the quantitative analysis of this invention, including, for example, phosphate buffers, Tris buffers and Good's buffers with a pH range of from 6 to 10. There is no special limitation on the temperature at which the reaction is conducted to the extent that $\Delta^4$DH may not be deactivated. Usually, a temperature of 20–40° C., preferably of close to 37° C., may be used.

The quantitation of 3-oxo-5$\beta$-steroid may be made, upon termination of the reaction by the addition of a terminating solution to the reaction mixture, by measuring the optical density of the colored substance in the mixture, or alternatively, by measuring the increase in the optical density of the colored substance in a prescribed period of time. Inorganic acids such as hydrochloric acid, sulfuric acid and phosphoric acid or organic acids such as citric acid and acetic acid may be used for a terminating solution.

The reagent for the quantitative analysis of this invention may be that consisting of a buffer solution added with 60–2,400 $\mu$mole/$\lambda$ of the reducing chromophoric agent and 60–12,000 units/$\lambda$ of $\Delta^4$DH. It is possible to prepare a buffer solution added with either one of the reducing chromophoric agent or $\Delta^4$DH in advance and to add the other when the reagent is used.

This invention makes use of the enzymes which are capable of specifically recognizing the structure of 3-oxo-5$\beta$-steroid and the colorimetry of the colored substance. The invention thus eliminates the need for the procedures on the samples such as a heat treatment, deproteinization and extraction, thus requiring only a small quantity of the samples, as much as 50–200 $\mu\lambda$ in one quantitation, and yet giving an excellent sensitivity.

The quantitative analysis of this invention can be applied to a loading test, in which a metabolism of dehydrochoric acid administered in a body is measured, thus providing a very simple and precise liver function test.

Other features of the invention will become apparent in the course of the following description of the exemplary embodiments which are given for illustration of the invention and are not intended to be limiting thereof.

EXAMPLES

Example 1

0.5 m$\lambda$ of 50 mmole/$\lambda$ phosphate buffer solution (pH8) containing 500 $\mu$mole/$\lambda$ NTB and 1,500 units/$\lambda$ $\Delta^4$DH (hereinafter referred to as "reagent") was added with 100 $\mu\lambda$ of samples, and reacted precisely for 10 minutes at 37° C., upon which 0.5 m$\lambda$ of the terminating solution (0.1N-HC$\lambda$) was added. After the resultant liquid was allowed to stand for 5 minutes, its optical density at a wave length of 540 nm was measured. The same samples were added to the reagent not containing $\Delta^4$DH and the above procedures were exactly repeated as a blank test. The samples used were serum added with dehydrochoric acid and diluted to various concentrations with the same serum but not containing dehydrochoric acid. $\Delta^4$DH used was that separated from Pseudomonas testosteroni cultured in accordance with the method proposed by Levy et al [J. Biol. Chem. 234, 2014 (1959)], and purified. The result obtained are shown in Table 1 below.

TABLE 1

| Dehydrochoric Acid Concentration (mole/l) | Optical Density at 540 nm |
|---|---|
| 20 | 0.022 |
| 40 | 0.046 |
| 60 | 0.077 |
| 80 | 0.101 |
| 100 | 0.122 |
| 140 | 0.172 |
| 180 | 0.226 |

Example 2

The same procedures were repeated on samples of serum added with in various concentrations the reagent of Example 1, but containing 5μ-androstan-3,17-dione (a methanol solution) instead of dehydrochloric acid. The result is shown in Table 2.

TABLE 2

| 5β-androstan-3,17-dione Concentration (mole/l) | Optical Density at 540 nm |
|---|---|
| 20 | 0.065 |
| 40 | 0.132 |
| 60 | 0.201 |
| 80 | 0.270 |
| 100 | 0.332 |
| 120 | 0.403 |

Example 3

A liver cirrhosis patient and a healthy subject were each intravenously given 1g of dehydrochoric acid. The changes of the dehydrochoric acid level in serum after the administration were determined according to the same procedure as in Example 1 and using the reagent of Example 1. The results are shown in the appended FIG. 1. The elimination constant (keλ), the half-life period (T ½) and the area under concentration curve of the compound in blood (AUC) are given in Table 3.

TABLE 3

| parameter | Healthy Subject | Liver Cirrhosis Patient |
|---|---|---|
| T1/2 (min) | 9.76 | 4.41 |
| Kel (min$^{-1}$) | 0.071 | 0.157 |
| AUC (μg · min/ml) | 2727 | 1398 |

Obviously, numerous modifications and variations of the present invention are possible in light of the above teachings. It is therefore to be understood that the scope of the appended claims, the invention may be practiced otherwise than as specifically described herein.

What is claimed as new and desired to be secured by letters patent of the United States is:

1. A method of quantitatively analyzing for a 3-oxo -5β-steroid, which comprises:

contacting a sample containing said steroid with 3-oxo-5-steroid-$\Delta^4$-dehydrogenase and a reducible, chromophoric tetrazolium agent and allowing the dehydrogenase to oxidize the steroid while at the same time reducing the chromophoric agent to a colored substance; and measuring the optical density of the colored substance thereby quantitatively analyzing for said 3-oxo-5-steroid.

2. The process of claim 1, wherein said chromophoric tetrazolium compound reagent is 3-(p indophenyl)-2-(p-nitrophenyl)-5-phenyl-2H-tetrazolium chloride, 3-(4,5-dimethyl-2-thiazolyl)-2,5-diphenyl-2H-tetrazolium bromide or 1,1'-(3,3'-dimethoxy-4,4'-biphenylene)-bis[5-(4-nitrophenyl)-3-[4-(2-hydroxy-3-(2-hydroxyethyldiethylamino)-propoxy)phenyl]]-2H-tetrazolium chloride.

3. The method of claim 1, wherein said 3-oxo-5β-steroid is dehydrochroric acid, 5β-androstan-3,17-dione, $\Delta^1$-5β-androstene-3,17-dione, 5β-pregnane-3,20-dione or 21-hydroxy-5β-pregnane-3,20-dione.

4. The method of claim 1, wherein the concentration of said tetrazolium compound in the analysis medium ranges from 50–2000 μmole/liter.

5. The method of claim 1, wherein the analysis reaction is conducted at a temperature of 20–40° C.

6. A reagent for the quantitative analysis of 3-oxo-5β-steroid, comprising:

3-oxo-5β-steroid-$\Delta^4$-dehydrogenase and a reducing, chromophoric tetrazolium compound agent.

* * * * *